(12) United States Patent
Eshoo

(10) Patent No.: US 10,202,642 B2
(45) Date of Patent: Feb. 12, 2019

(54) DNA SEQUENCING

(71) Applicant: IBIS BIOSCIENCES, INC., Carlsbad, CA (US)

(72) Inventor: Mark W. Eshoo, San Diego, CA (US)

(73) Assignee: IBIS BIOSCIENCES, INC., Carlsbad, CA (US)

(*) Notice: Subject to any disclaimer, the term of this patent is extended or adjusted under 35 U.S.C. 154(b) by 157 days.

(21) Appl. No.: 14/398,267

(22) PCT Filed: May 2, 2013

(86) PCT No.: PCT/US2013/039295
§ 371 (c)(1),
(2) Date: Oct. 31, 2014

(87) PCT Pub. No.: WO2013/166303
PCT Pub. Date: Nov. 7, 2013

(65) Prior Publication Data
US 2015/0184238 A1    Jul. 2, 2015

Related U.S. Application Data

(60) Provisional application No. 61/641,715, filed on May 2, 2012, provisional application No. 61/787,437, filed on Mar. 15, 2013.

(51) Int. Cl.
C12Q 1/68        (2018.01)
C12Q 1/6869      (2018.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| | | |
|---|---|---|
| 3,996,345 A | 12/1976 | Ullman et al. |
| 4,351,760 A | 9/1982 | Khanna et al. |
| 4,415,732 A | 11/1983 | Caruthers et al. |
| 4,458,066 A | 7/1984 | Caruthers et al. |
| 4,683,195 A | 7/1987 | Mullis et al. |
| 4,683,202 A | 7/1987 | Mullis |
| 4,725,677 A | 2/1988 | Koester et al. |
| 4,739,044 A | 4/1988 | Stabinsky |
| 4,757,141 A | 7/1988 | Fung et al. |
| 4,889,818 A | 12/1989 | Gelfand et al. |
| 4,973,679 A | 11/1990 | Caruthers et al. |
| 4,980,460 A | 12/1990 | Molko et al. |
| 5,695,934 A | 12/1997 | Brenner |
| 5,714,330 A | 2/1998 | Brenner et al. |
| 5,750,341 A | 5/1998 | Macevicz |
| 5,912,148 A | 6/1999 | Eggerding |
| 6,001,983 A * | 12/1999 | Benner .................. C07H 21/00 435/91.1 |
| 6,130,073 A | 10/2000 | Eggerding |
| 6,210,891 B1 | 4/2001 | Nyren et al. |
| 6,258,568 B1 | 7/2001 | Nyren |
| 6,306,597 B1 | 10/2001 | Macevicz |
| 6,329,178 B1 | 12/2001 | Patel et al. |
| 6,395,524 B2 | 5/2002 | Loeb et al. |
| 6,432,360 B1 | 8/2002 | Church |
| 6,485,944 B1 | 11/2002 | Church et al. |
| 6,511,803 B1 | 1/2003 | Church et al. |
| 6,602,695 B2 | 8/2003 | Patel et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,315,019 B2 | 1/2008 | Turner et al. |
| 7,329,492 B2 | 2/2008 | Hardin et al. |

(Continued)

FOREIGN PATENT DOCUMENTS

| | | |
|---|---|---|
| EP | 0320308 B1 | 11/1993 |
| WO | 93/05176 | 3/1993 |

(Continued)

OTHER PUBLICATIONS

Maxam and Gilbert, PNAS 74: 560-564, 1977.*
Examination Report dated Apr. 11, 2016 for European Application No. EP13784766 filed May 2, 2013.
International Search Report and Written Opinion for Application No. PCT/US2013/039295, dated Oct. 8, 2013, 18 pages.
Kirzhner V., et al., "Different Clustering of Genomes Across Life Using the A-T-C-G and Degenerate R-Y Alphabets: Early and Late Signaling on Genome Evolution?," Journal of Molecular Evolution, 2007, vol. 64 (4), pp. 448-456.
Maxam A.M., et al., "A New Method for Sequencing DNA," Proceedings of the National Academy of Sciences of the United States of America, 1977, vol. 74 (2), pp. 560-564.
Nikolaeva S.L., et al., The Purine-Pyrimidine Classification Scheme Reveals New Patterns in the Genetic Code, 2005 [online]. Retrieved from the Internet:.

(Continued)

*Primary Examiner* — Suryaprabha Chunduru
(74) *Attorney, Agent, or Firm* — Casimir Jones, S.C.; Kirk Hogan

(57) ABSTRACT

Provided herein is technology relating to sequencing nucleic acids and particularly, but not exclusively, to methods, compositions, systems, and kits for sequencing a nucleic acid using a degenerate two-base code. Particular embodiments provide: 1) that the two-base degenerate code relates a first element to a base comprising adenine (A) or guanine (G) and a second element to a base comprising cytosine (C) or thymine (T); 2) that the two-base degenerate code relates a first element to a base comprising A or C and a second element to a base comprising G or T; and 3) that the two-base degenerate code relates a first element to a base comprising G or C and a second element to a base comprising A or T.

13 Claims, 3 Drawing Sheets

Specification includes a Sequence Listing.

(56) References Cited

U.S. PATENT DOCUMENTS

| | | |
|---|---|---|
| 7,405,281 B2 | 7/2008 | Xu et al. |
| 7,476,503 B2 | 1/2009 | Turner et al. |
| 7,482,120 B2 | 1/2009 | Buzby et al. |
| 7,501,245 B2 | 3/2009 | Quake et al. |
| 7,563,576 B2 | 7/2009 | Chee et al. |
| 7,668,697 B2 | 2/2010 | Volkov et al. |
| 2006/0051807 A1 | 3/2006 | Fuller |
| 2007/0036511 A1 | 2/2007 | Lundquist et al. |
| 2007/0048748 A1 | 3/2007 | Williams et al. |
| 2007/0072196 A1 | 3/2007 | Xu et al. |
| 2007/0077564 A1 | 4/2007 | Roitman et al. |
| 2007/0128133 A1 | 6/2007 | Eid et al. |
| 2007/0134128 A1 | 6/2007 | Korlach |
| 2007/0141598 A1 | 6/2007 | Turner et al. |
| 2007/0161017 A1 | 7/2007 | Eid et al. |
| 2007/0166705 A1 | 7/2007 | Milton et al. |
| 2007/0172824 A1* | 7/2007 | Chun .............. C12Q 1/686 435/6.11 |
| 2007/0188750 A1 | 8/2007 | Lundquist et al. |
| 2007/0196846 A1 | 8/2007 | Hanzel et al. |
| 2007/0206187 A1 | 9/2007 | Lundquist et al. |
| 2007/0231804 A1 | 10/2007 | Korlach et al. |
| 2007/0238679 A1 | 10/2007 | Rank et al. |
| 2008/0009007 A1 | 1/2008 | Lyle et al. |
| 2008/0026951 A1 | 1/2008 | Brown et al. |
| 2008/0030628 A1 | 2/2008 | Lundquist et al. |
| 2008/0032301 A1 | 2/2008 | Rank et al. |
| 2008/0050747 A1 | 2/2008 | Korlach et al. |
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2011/0202280 A1* | 8/2011 | Sikora .............. C12Q 1/6874 702/19 |

FOREIGN PATENT DOCUMENTS

| | | |
|---|---|---|
| WO | 9305176 A1 | 3/1993 |
| WO | WO 93/19205 * | 3/1993 |
| WO | 93/19205 | 9/1993 |
| WO | 9319205 A1 | 9/1993 |
| WO | WO 96/12822 * | 10/1995 |
| WO | 96/12822 | 5/1996 |
| WO | 9612822 A1 | 5/1996 |
| WO | WO-0018957 A1 | 4/2000 |
| WO | WO-2004018497 A2 | 3/2004 |
| WO | WO-2005123957 A2 | 12/2005 |
| WO | WO-2006084132 A2 | 8/2006 |
| WO | 2007/106690 | 9/2007 |
| WO | 2007106690 A2 | 9/2007 |
| WO | WO-2009154733 A2 | 12/2009 |
| WO | 2010117804 A2 | 10/2010 |
| WO | 2010/127304 | 11/2010 |

OTHER PUBLICATIONS

Supplementary European Search Report for Application No. EP13784766, dated Dec. 23, 2015, 11 pages.

Abraham M.L., et al., "Nucleobase Analogs for Degenerate Hybridization Devised Through Conformational Pairing Analysis," Biotechniques, 2007, vol. 43 (5), pp. 617-624.

Adessi C., et al., "Solid Phase DNA Amplification: Characterisation of Primer Attachment and Amplification Mechanisms," Nucleic Acids Research, 2000, vol. 28 (20), pp. E87.

Agrawal S., et al., "Site-Specific Functionalization of Oligodeoxynucleotides for Non-Radioactive Labelling," Tetrahedron Letters, 1990, vol. 31 (11), pp. 1543-1546.

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

Beaucage S.L., et al., "Advances in the Synthesis of Oligonucleotides by the Phosphoramidite Approach," Tetrahedron, 1992, vol. 48 (12), pp. 2223-2311.

Bennett S.T., et al., "Toward the 1,000 Dollars Human Genome," Pharmacogenomics, 2005, vol. 6 (4), pp. 373-382.

Bentley D.R., et al., "Accurate Whole Human Genome Sequencing Using Reversible Terminator Chemistry," Nature, 2008, vol. 456 (7218), pp. 53-59.

Berlman, "Handbook of Fluorescence Spectra of Aromatic Molecules," 2nd edition, Academic Press, New York, 1971.

Birren, et al., Genome Analysis: Analyzing DNA, Cold Spring Harbor, N.Y., 1997.

Bishop, Ed., "Indicators," Pergamon Press, Oxford, 1972.

Braslavsky I., et al., "Sequence Information can be Obtained from Single DNA Molecules," Proceedings of the National Academy of Sciences, 2003, vol. 100 (7), pp. 3960-3964.

Brenner S., et al., "Gene Expression Analysis by Massively Parallel Signature Sequencing (MPSS) on Microbead Arrays," Nature Biotechnology, 2000, vol. 18 (6), pp. 630-634.

Eckstein F., Oligonucleotides and Analogues, IRL Press, 1991, Table of Contents.

Fuller C.W., et al., "The Challenges of Sequencing by Synthesis," Nature Biotechnology, 2009, vol. 27 (11), pp. 1013-1023.

Griffiths, Colour and Constitution of Organic Molecules, Academic Press, New York, 1976.

Guo J., et al., "Four-Color DNA Sequencing With 3'-O-Modified Nucleotide Reversible Terminators and Chemically Cleavable Fluorescent Dideoxynucleotides," Proceedings of theNational Academyof Sciences, 2008, vol. 105 (27), pp. 9145-9150.

Gyllensten U.B., et al., "Generation of Single-Stranded DNA by the Polymerase Chain Reaction and its Application to Direct Sequencing of the Hla-Dqa Locus," Proceedings of the National Academy of Sciences of the United States of America, 1988, vol. 85 (20), pp. 7652-7656.

Harris T.D., et al., "Single-molecule DNA Sequencing of a Viral Genome," Science, 2008, vol. 320 (5872), pp. 106-109.

Haugland, Handbook of Fluorescent Probes and Research Chemicals, Molecular Probes, Eugene, 1992.

Innis M.A., et al., PCR Protocols—A Guide to Methods and Applications, Academic Press Inc., 1990, Table of Contents.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

(56) References Cited

OTHER PUBLICATIONS

Kricka et al., "Molecular Probing, Blotting, and Sequencing," especially Chapter 1 Labels, Labeling, Analytical Strategies, and Applications and Table IX, Academic Press, New York, 1995.
Lin P.K., et al., "Synthesis of Oligodeoxyribonucleotides Containing Degenerate Bases and their Use as Primers in the Polymerase Chain Reaction," Nucleic Acids Research, 1992, vol. 20 (19), pp. 5149-5152.
Loh E.Y., et al., "Polymerase Chain Reaction With Single-Sided Specificity: Analysis of T Cell Receptor Delta Chain," Science (New York, N.Y.), 1989, vol. 243 (4888), pp. 217-220.
MacLean D., et al., "Application of 'next-generation' Sequencing Technologies to Microbial Genetics," Nature Reviews Microbiology, 2009, vol. 7 (4), pp. 287-296.
Mardis E.R., "Next-Generation DNA Sequencing Methods," Annual Review of Genomics and Human Genetics, 2008, vol. 9, pp. 387-402.
Margulies M., et al., "Genome Sequencing in Microfabricated High-Density Picolitre Reactors," Nature, 2005, vol. 437 (7057), pp. 376-380.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Moyer P., et al., "Near-Field Optical Microscopes Break the Diffraction Limit," Laser Focus World, 1993, vol. 29, 6 pages.
Nelson P.S., et al., "Bifunctional Oligonucleotide Probes Synthesized Using a Novel CPG Support are able to Detect Single Base Pair Mutations," Nucleic Acids Research, 1989, vol. 17 (18), pp. 7187-7194.
Ochman H., et al., "Genetic Applications of an Inverse Polymerase Chain Reaction," Genetics, 1988, vol. 120 (3), pp. 621-623.
Pennisi E., "Genomics. Semiconductors Inspire New Sequencing Technologies," Science, 2010, vol. 327 (5970), pp. 1190.
Pringsheim, Fluorescence and Phosphorescence, Interscience Publishers, New York, 1949.
Ronaghi M., et al., "A sequencing method based on real-time pyrophosphate," Science, 1998, vol. 281 (5375), pp. 363-365.
Sambrook J., et al., eds., Molecular Cloning: A Laboratory Manual, 3rd Edition, Cold Spring Harbor Laboratory, 2001, Table of Contents.
Seo T.S., et al., "Four-color DNA Sequencing by Synthesis on a Chip Using Photocleavable Fluorescent Nucleotides," Proceedings of the National Academy of Sciences of the United States of America, 2005, vol. 102 (17), pp. 5926-5931.
Sharma P., et al., "A General Method for the Synthesis of 3'-Sulfhydryl and Phosphate Group Containing Oligonucleotides," Nucleic Acids Research, 1991, vol. 19 (11), pp. 3019-3025.
Shendure J., et al., "Accurate Multiplex Polony Sequencing of an Evolved Bacterial Genome," Science, 2005, vol. 309 (5741), pp. 1728-1732.
Sproat B.S., et al., "The Synthesis of Protected 5'-Mercapto-2',5'-Dideoxyribonucleoside-3'-0-Phosphorainidites; Uses of 5'-Mercapto-Oligodeoxyribonucleotides," Nucleic Acids Research, 1987, vol. 15 (12), pp. 4837-4848.
Stickland J.E., et al., "Quantification of Oncogene Dosage in Tumours by Simultaneous Dual-Label Hybridization," Oncogene, 1993, vol. 8 (1), pp. 223-227.
Turcatti G., et al., "A New Class of Cleavable Fluorescent Nucleotides: Synthesis and Optimization as Reversible Terminators for DNA Sequencing by Synthesis," Nucleic Acids Research, 2008, vol. 36 (4), pp. e25.
Voelkerding K.V., et al., "Next-Generation Sequencing: from Basic Research to Diagnostics," Clinical Chemistry, 2009, vol. 55 (4), pp. 641-658.
Wu W., et al., "Termination of DNA Synthesis by N6-Alkylated, Not 3'-O-Alkylated, Photocleavable 2'-Deoxyadenosine Triphosphates," Nucleic Acids Research, 2007, vol. 35 (19), pp. 6339-6349.
Zuckermann R., et al., "Efficient Methods for Attachment of Thiol Specific Probes to the 3'-Ends of Synthetic Oligodeoxyribonucleotides," Nucleic Acids Research, 1987, vol. 15 (13), pp. 5305-5321.
Communication mailed by European Patent Office in European application No. 13784766.1 dated Mar. 20, 2017.
Maxam A M et al., A new method for sequencing DNA, Proceedings of the National Academy of Sciences of the USA, New York, NY, US, vol. 74, No. 2, Feb. 1, 1977, pp. 560-564.

* cited by examiner

Fig. 1A aactgagcggcagcagcgagacctggcctactgtgtgtcacagctgcccctcacagagcgaggcctccgtaagat
gcttgacaatttgactgttttggagacaaactgtcagatgagtccatcttcagtgcttttttgtcagttgtagg
caagctgcgacgtggggccaagcctgagggcaag (SEQ ID NO. 1)

Fig. 1B rryyrrryrryrryrryrrryyyrryyyrgyryryryrgyryrryrgyyyyyyrgyrrrryrrrryyyyyrgyrrrry
ryyyrryrryyyyrryyryyyyrrrrryrrryyryyrrryrrryyyrgyyyyyryyryyyyyyyryyryyryrrr
yrrryyryrryryrrryyrrryyyrrrrrryrrr (SEQ ID NO. 2)

Fig. 1C mmmkkmkmkkmmkmmkmkmkmmmkkkmmkmmkkkkkkkmmmmkmkkmmmmkmmmmkmkmkmkkmmkmmkkmmkmk
kmkkkmmmmkkkkkmmkkkkkkkmkmmmmmmkkkmmkmkkmkkmmmkmkkmmkkkmkkkkkkkkmmkkkkkmkk
mmmkmkkmkmmkkkkkkmmmmkmmkkmkkkmmmk (SEQ ID NO. 3)

Read 2.1 observed sequence

CTTCTATCGGATTTTTAAGGCAAGGCAAGGGCTCCGAAAATATTTAACCCGGAGGCCCGGCAGCAATCGCATCAACTACCGGC
GAGCTACGAATAGACGCCGGCCAGGCAAATCATTATTACGGGACCCAGGGCTAAGATCAACAAATAGGCAAGGCGGGAGGATT
GATTCGCCGCTCGA  (SEQ ID NO. 4)

degenerate sequence

CKKCKAKCKKAKKKKAAKKCAAKKCAAKKKCKCCKAAAAKAKKKAACCCKKAKKCCCKKCAKCAAKCKCAKCAACKACCKKC
KAKCKACKAAKAKACKCCKKCCAKKCAAAKCAKKAKKACKKKACCCAKKKCKAAKAKCAACAAAKAKKCAAKKCKKKAKKAKK
KAKKCKCCKCKCKA  (SEQ ID NO. 5)

Homology identified over 180 bases (94% accuracy)

degenerate sequence

```
CKKCKAKCKKAKKKKAAKKCAAKKCAAKKKCKCCKAAAAKAKKKAA-CCCKKAKKCCCKKCAKCAAKCK
||||||||||||||||||||||||||||||||||||||||||| |||| ||||||| |||||||||
CTGCGAGCTTATTGTTAAGGCAATGCAAGGTCTCCTAAAAGATGGAAACCCG-ATTCCCT-CAGCAATCG
```
MS2 Sequence degenerate sequence (continued)

```
-AKCAACKACCKKCKAKCKACKAAKAKACKCCKKCCAKKCAAAKCAKKAKKACKKKACCCAKKKCKAAKA
 |||||   ||||| |||||||||||||||||||||||||||||||||  ||||||||||||||||
CAGCAAACTCCGGC-ATCTACTAATAGACGCCGGCCATTCAAA-CATGAGGA--TTACCCATGTCGAAGA
```
MS2 Sequence (continued)

degenerate sequence (continued)

```
KCAACAAAKA-KK-CAAKKCKKKAKK-AKKKAKKCKCCKCKCKA  (SEQ ID NO. 6)
|||||||||| || ||| |||||||| ||||||  ||||||||
-CAACAAAGAAGTTCAACTCTTTATGTATTGATCTTCCTCGCGA  (SEQ ID NO. 7)
```
MS2 Sequence (continued)

Fig. 2

Read 3.1 observed sequence

AGATTTAATTACGAACGCCAGGCTTCGACATTAAGCTCGACACCACCAACATTCGGGGGGGGCCTACGGAGGGCAGCCTCGAC
GGGATTTTTAGGGGCTAGGGGCGGGCTCATATCGCGGACGAAGCTACATTTACGGGGAATTCCGGGGAACGCGGAGGGTTATT
CGATCGCTAGCGAGCCCTTATCGAATT (SEQ ID NO. 8)

degenerate sequence

AKAKKKAAKKACKAACKCCAKKCKKCKACAKKAAKCKCKACACCACCAACAKKCKKKKKKKKCCKACKKAKKKCAKCCKCKAC
KKKAKKKKKAKKKKCKAKKKKCKKKCKCAKAKCKCKKACKAAKCKACAKKKACKKKKAAKKCCKKKKAACKCKKAKKKKKAKK
CKAKCKCKAKCKAKCCCKKAKCKAAKK (SEQ ID NO. 9)

Homology identified over 193 bases (90% accuracy)

degenerate sequence (continued)

```
AKAKKKAAKKACKAACKCCAKKCKKCKACAKKAAKCKCKACACCACCAACAKKCKKKKKKKKCCKACKK-
||||||||||||||||||||||||||||||||||||||||||||||||||||||||||||| || |||||
ATATTTAAGTACGAACGCCATGCGGCTACAGGAAGCTCTACACCACCAACAGTCTGGTTG-CC-ACTTT
```
MS2 Sequence degenerate sequence

```
AKKKCAKCCKCKACKKK-AKKKKK-AKKKKCKAKKKKCKKKCKCAKAKCKCKKACKAA-KCKACAKKK-A
||| || |||||||||||||||||||||||||||   ||||||||||||||||| ||||||||| |
AGG-CA-CCTCGACTTTGATGGTGTATTTGCGATTCT---GCGCAGAGCTCTGACGAACGCTACAGGTTA
```
MS2 Sequence degenerate sequence

```
CKKKK-AAKKCCKKKKAACKCKKAKKKKKAKKCKAKC--KCKAKCKAKCCC-KKAKCKAAKK  (SEQ ID NO. 11)
||||| ||| ||||||||||||| |||||||| |||| | ||||| ||| |||||||||||
CTTTGTAAG-CCTGTGAACGCG-AGTTAGAGCTGATCCATTCAGCGACCCCGTTAGCGAAGT  (SEQ ID NO. 10)
```
MS2 Sequence

Fig. 3

DNA SEQUENCING

CROSS-REFERENCE TO RELATED APPLICATIONS

The present Application claims priority to U.S. Provisional Application Ser. No. 61/641,715 filed 2 May 2012, and U.S. Provisional Application Ser. No. 61/787,437 filed 15 Mar. 2013, the entirety of each of which is incorporated by reference herein.

FIELD OF INVENTION

Provided herein is technology relating to sequencing nucleic acids and particularly, but not exclusively, to methods, compositions, and systems for sequencing a nucleic acid using a degenerate two-base code.

BACKGROUND

DNA sequencing is driving genomics research and discovery. The completion of the Human Genome Project was a monumental achievement involving an incredible amount of combined efforts among genome centers and scientists worldwide. This decade-long project was completed using the Sanger sequencing method to determine the order of the four nucleotide bases-adenine, guanine, cytosine, and thymine—in molecules of DNA. This method remains the staple genome sequencing methodology in high-throughput genome sequencing centers. In addition, many "next-generation" sequencing platforms have been established as practical alternatives to the Sanger method and are in wide use. These include sequencing-by-synthesis (SBS) approaches such as pyrosequencing (Ronaghi et al. (1998) *Science* 281: 363-365), sequencing of single DNA molecules (Braslaysky et al. (2003) *Proc. Natl. Acad. Sci USA* 100: 3960-3964), and polymerase colonies ("polony" sequencing) (Mitra et al. (2003) *Anal. Biochem.* 320: 55-65). While the fundamental technologies of the various extant and nascent sequencing methods may differ greatly, conventional sequencing methods share the feature of providing a sequence in terms of the four nucleotide bases adenine, guanine, cytosine, and thymine (or, in RNA, uracil).

SUMMARY

Conventional methods of sequencing by synthesis are based on differentially identifying the four bases A, C, G, and T that are incorporated into a nucleic acid during each base incorporation event during synthesis. In contrast, the present technology is based on sequencing nucleic acids using a two-base degenerate code. For example, rather than determining the sequence of the four bases in a nucleic acid, the present technology in some embodiments determines the order of purine and pyrimidine bases in a nucleic acid. Using a sequencing scheme according to this exemplary approach, the conventionally derived sequence ACGT would instead be acquired by determining that the sequence consists of a purine in the first position, a pyrimidine in the second position, a purine in the third position, and a pyrimidine in the fourth position, which may be represented as RYRY. An alternative two-base sequencing scheme based on identifying the sequence of keto bases and amino bases produces the sequence of MMKK for this same four-base sequence of bases ACGT. In some embodiments, the information of the two two-base sequences can be merged to produce a conventional four-base sequence. According to the current example, the first position is an amino purine base, the second position is an amino pyrimidine base, the fourth position is a keto purine base, and the fourth position is a keto pyrimidine base, which leads unambiguously to the sequence ACGT.

As a consequence, embodiments of the technology require fewer flows of nucleotide solutions and/or wash steps for each synthesis cycle, which thus also reduces the time for acquiring a sequence and reduces the complexity and cost of apparatuses used for the types of sequencing schemes described herein. In addition, some embodiments of the technology reduce the number of fluorescent dyes needed for sequencing, thus also reducing the number of lasers used to excite labels (e.g., fluorescent moieties), reducing or eliminating optics used to split the optical signal by wavelength, and reducing of the number of detectors for recording incorporation events and differentiating between bases.

Accordingly, provided herein are methods for sequencing a target nucleic acid, the method comprising choosing a two-base degenerate code; and determining a two-base degenerate sequence of the target nucleic acid using the two-base degenerate code. A two-base degenerate code can be based on various classifications and properties of the conventional bases A, C, G, and T (or U). For example, in some embodiments the two-base degenerate code represents the order of purine bases and pyrimidine bases (e.g., as R and Y); in some embodiments, the two-base degenerate code represents the order of keto bases and amino bases (e.g., K and M); and in some embodiments the two-base degenerate code represents the order of strongly hydrogen bonding bases and weakly hydrogen bonding bases (e.g., S and W). Particular embodiments provide: 1) that the two-base degenerate code relates a first element to a base comprising adenine (A) or guanine (G) and a second element to a base comprising cytosine (C) or thymine (T); 2) that the two-base degenerate code relates a first element to a base comprising A or C and a second element to a base comprising G or T; and 3) that the two-base degenerate code relates a first element to a base comprising G or C and a second element to a base comprising A or T.

Sequences using different two-base degenerate codes can be used in combination to derive a standard four-base nucleotide sequence for a nucleic acid. Accordingly, some embodiments of the technology provide a method comprising merging a first two-base degenerate sequence and a second two-base degenerate sequence to produce a four-base sequence.

Embodiments of methods according to the technology comprise providing a first nucleotide and a second nucleotide wherein the first nucleotide is labeled with a label and the second nucleotide is labeled with said label. Furthermore, some embodiments comprise providing a first nucleotide, a second nucleotide, a third nucleotide, and a fourth nucleotide, wherein the first nucleotide is labeled with a first label, the second nucleotide is labeled with said first label, the third nucleotide is labeled with a second label, and the fourth nucleotide is labeled with said second label.

In addition, some embodiments comprise providing a labeled nucleotide analogue wherein the labeled nucleotide analogue base pairs with a first nucleotide or a second nucleotide. Moreover, embodiments also comprise providing a first labeled nucleotide analogue and a second labeled nucleotide analogue wherein the first labeled nucleotide analogue base pairs with a first nucleotide or a second nucleotide and the second labeled nucleotide analogue base pairs with a third nucleotide or a fourth nucleotide.

In some embodiments, determining a two-base degenerate sequence of the target nucleic acid using the two-base degenerate code comprises measuring a physical, chemical, and/or electronic characteristic of a base and differentiating between a purine base and a pyrimidine base, between a keto base and an amino base, and/or between a strongly hydrogen bonding base (e.g., a base pair consisting of three hydrogen bond pairs) and a weakly hydrogen bonding base (e.g., a base pair consisting of two hydrogen bond pairs).

In some embodiments, the two-base sequence of the target nucleic acid is compared to a known sequence, e.g., to detect a change in the nucleotide sequence (e.g., a single nucleotide polymorphism, an insertion, a deletion, a splice site variation, a transition, a transversion, a missense mutation, a nonsense mutation, etc.). In some embodiments, the known sequence identifies all bases (a, t, c, g, and u) and is converted (e.g., by a computer) to a 2-base code.

Also provided are compositions related to sequencing a nucleic acid using a two-base degenerate code. For instance, some embodiments provide a composition comprising a first nucleotide and a second nucleotide wherein the first nucleotide is labeled with a first label and the second nucleotide is labeled with said first label. In some embodiments, the label is a fluorescent moiety. Some embodiments of compositions provide four nucleotides for sequencing using a degenerate two-base code. In particular, embodiments provide a third nucleotide and a fourth nucleotide, wherein the third nucleotide is labeled with a second label and the fourth nucleotide is labeled with said second label. In some embodiments, the first nucleotide is an A, the second nucleotide is a G, the third nucleotide is a C, and the fourth nucleotide is a T. In some embodiments, the first nucleotide is an A, the second nucleotide is a C, the third nucleotide is a G, and the fourth nucleotide is a T. Furthermore, in some embodiments the first nucleotide is a C, the second nucleotide is a G, the third nucleotide is an A, and the fourth nucleotide is a T.

The compositions provided herein relate to sequencing a nucleic acid; as such, the technology includes embodiments of compositions comprising a target nucleic acid, a sequencing primer, and a polymerase. Upon incorporation of a nucleotide, e.g., in a sequencing reaction, the compositions in some embodiments comprise a nucleic acid comprising the first nucleotide and/or the second nucleotide.

The methods and compositions of the technology find use in systems for sequencing a nucleic acid using a degenerate two-base code. In one aspect, the technology provides embodiments of a system for sequencing a nucleic acid, the system comprising a sequencing apparatus and a functionality to differentiate a first nucleotide and a second nucleotide from a third nucleotide and a fourth nucleotide. In some embodiments, the system further comprises an output functionality to provide a degenerate two-base nucleotide sequence of the nucleic acid. Sequences using different degenerate two-base codes can be merged to provide a four-base code for a nucleic acid; that is, some embodiments comprise a functionality to merge a first degenerate two-base nucleotide sequence of the nucleic acid and a second degenerate two-base nucleotide sequence of the nucleic acid to provide a four-base sequence of the nucleic acid. In addition, embodiments of the technology relate to a system wherein the functionality to differentiate a first nucleotide and a second nucleotide from a third nucleotide and a fourth nucleotide differentiates between a purine base and a pyrimidine base, between a keto base and an amino base, and/or between a strongly hydrogen bonding base and a weakly hydrogen bonding base.

In one aspect, the 2-base code is determined (e.g., by sequencing) without determining and/or otherwise knowing the 4-base code.

Embodiments of kits are provided, e.g., a kit for sequencing a nucleic acid, the kit comprising a first nucleotide, a second nucleotide, a third nucleotide, and a fourth nucleotide, wherein the first nucleotide is labeled with a first label, the second nucleotide is labeled with said first label, the third nucleotide is labeled with a second label, and the fourth nucleotide is labeled with said second label; or a first two-base degenerate nucleotide analogue and a second two-base degenerate nucleotide analogue, wherein the first nucleotide analogue is labeled with a first label and the second nucleotide analogue is labeled with a second label. Additional embodiments will be apparent to persons skilled in the relevant art based on the teachings contained herein.

BRIEF DESCRIPTION OF THE DRAWING

These and other features, aspects, and advantages of the present technology will become better understood with regard to the following drawings:

FIG. 1A shows a conventional four-base sequence from the *Homo sapiens* glyceraldehyde 3-phosphate dehydrogenase gene. FIG. 1B shows this sequence represented using a two-base degenerate code of "r" and "y" denoting the order of purines and pyrimidines, respectively. FIG. 1C shows this sequence represented using a two-base degenerate code of "m" and "k" denoting the order of amino and keto bases, respectively. In FIG. 1, r=A or G, y=C or T, m=A or C, and k=G or T.

FIG. 2 shows a sequence read acquired according to the technology provided herein. The "observed sequence" (SEQ ID NO: 4) is the sequence read generated by the Ion Torrent sequencer under standard conditions. The "degenerate sequence" (SEQ ID NO: 5) was generated under the experimental conditions in which the Gs and Ts were mixed together and used in place of both G and T. The degenerate sequence is shown using the degenerate single letter code of K, which denotes a position in which is found G or T. The indicated "homology" denotes the matching of the "degenerate sequence" to the MS2 genome. For read 2.1, alignment of the read to the MS2 genome identified over 180 bases, which corresponds to an accuracy of 94%.

FIG. 3 shows a sequence read acquired according to the technology provided herein. The "observed sequence" (SEQ ID NO: 8) is the sequence read generated by the Ion Torrent sequencer under standard conditions. The "degenerate sequence" (SEQ ID NO: 9) was generated under the experimental conditions in which the Gs and Ts were mixed together and used in place of both G and T. The degenerate sequence is shown using the degenerate single letter code of K, which denotes a position in which is found G or T. The indicated "homology" denotes the matching of the "degenerate sequence" to the MS2 genome. For read 3.1, alignment of the read to the MS2 genome identified over 193 bases, which corresponds to an accuracy of 90%.

DETAILED DESCRIPTION

Provided herein is technology relating to sequencing nucleic acids and particularly, but not exclusively, to methods, compositions, systems, and kits for sequencing a nucleic acid using a degenerate two-base code.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligonucleotide or polynucleotide chemistry and hybridization described herein are those well known and commonly used in the art. Unless otherwise indicated, standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. (2000)). The nomenclatures utilized in connection with, and the laboratory procedures and techniques described herein are those well known and commonly used in the art.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

A "system" denotes a set of components, real or abstract, comprising a whole where each component interacts with or is related to at least one other component within the whole.

As used herein, the phrase "dNTP" means deoxynucleotidetriphosphate, where the nucleotide comprises a nucleotide base, such as A, T, C, G or U. In addition, the term "dNTP" is intended to refer also to deoxynucleotidetriphosphates comprising modified bases and base analogues that are capable of mimicking the base pairing of A, C, G, T, or U, or that are capable of base pairing in a degenerate mode, e.g., a base that pairs with A or G, C or T, A or C, G or T, G or C, or A or T.

The term "monomer" as used herein means any compound that can be incorporated into a growing molecular chain by a given polymerase. Such monomers include, without limitations, naturally occurring nucleotides (e.g., ATP, GTP, TTP, UTP, CTP, dATP, dGTP, dTTP, dUTP, dCTP, synthetic analogs), precursors for each nucleotide, non-naturally occurring nucleotides and their precursors, or any other molecule that can be incorporated into a growing polymer chain by a given polymerase.

As used herein, a "nucleic acid" shall mean any nucleic acid molecule, including, without limitation, DNA, RNA and hybrids thereof. The nucleic acid bases that form nucleic acid molecules can be the bases A, C, G, T and U, as well as derivatives and analogues thereof. Derivatives of these bases are well known in the art. The term should be understood to include, as equivalents, analogs of either DNA or RNA made from nucleotide analogs. The term as used herein also encompasses cDNA, that is complementary, or copy, DNA produced from an RNA template, for example by the action of reverse transcriptase. It is well known that DNA (deoxyribonucleic acid) is a chain of nucleotides consisting of 4 types of nucleotides—A (adenine), T (thymine), C (cytosine), and G (guanine)—and that RNA (ribonucleic acid) is a chain of nucleotides consisting of 4 types of nucleotides—A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. As used herein, "nucleic acid sequencing data", "nucleic acid sequencing information", "nucleic acid sequence", "genomic sequence", "genetic sequence", "fragment sequence", or "nucleic acid sequencing read" denotes any information or data that is indicative of the order of the nucleotide bases in a molecule (e.g., a whole genome, a whole transcriptome, an exome, oligonucleotide, polynucleotide, fragment, etc.) of DNA or RNA using a four-base code (e.g., using A, G, C, and T or U to represent the four bases adenine, guanine, cytosine, and thymine or uracil) or a two-base degenerate code to represent purine and pyrimidine bases; keto and amino bases; and/or strongly hydrogen bonding and weakly hydrogen bonding bases.

The IUB degenerate codes for nucleotide bases are used herein. In this code, R means either of the purine bases A or G; Y means either of the pyrimidine bases C or T; M means either of the amino bases A or C; K means either of the keto bases G or T; S means either of the stronger hydrogen binding partners C or G; and W means either of the weaker hydrogen bonding partners A or T.

Reference to a base, a nucleotide, or to another molecule may be in the singular or plural. That is, a base may refer to a single molecule of that base or to a plurality of that base, e.g., in a solution.

As used herein, a "polynucleotide", also called a nucleic acid, is a covalently linked series of nucleotides in which the 3' position of the pentose of one nucleotide is joined by a phosphodiester group to the 5' position of the next. DNA (deoxyribonucleic acid) and RNA (ribonucleic acid) are biologically occurring polynucleotides in which the nucleotide residues are linked in a specific sequence by phosphodiester linkages. As used herein, the terms "polynucleotide" or "oligonucleotide" encompass any polymer compound having a linear backbone of nucleotides. An "oligodeoxyribonucleotide" or "oligonucleotides", also termed an "oligomer", is generally a polynucleotide of a shorter length.

In this disclosure, "DNA", "oligonucleotide", or "nucleic acid" is understood to include DNA and RNA, as well as derivatives where the sugar is modified, as in 2'-O-methyl and 2', 3'-dideoxynucleoside derivatives, where the nucleobase has an appendage, and these nucleic acids and their analogs in non-linear topologies, including as dendrimers, comb-structures, and nanostructures, and analogs carrying appendages or tags (e.g., fluorescent, functionalized, or binding, such as biotin).

As used herein, the phrase "a clonal plurality of nucleic acids" or "a clonal population of nucleic acids" or "a cluster" or "a polony" refers to a set of nucleic acid products that are substantially or completely or essentially identical to each other, and they are complementary copies of the template nucleic acid strand from which they are synthesized.

As used herein, a "two-base nucleotide analogue" is a nucleotide analogue that can base pair with two different nucleotide bases of the set A, C, G, and T (or U).

As used herein, "complementary" generally refers to specific nucleotide duplexing to form canonical Watson-Crick base pairs, as is understood by those skilled in the art. However, complementary also includes base-pairing of modified nucleotides and nucleotide analogues that are capable of degenerate or universal base-pairing with A, T, G or C nucleotides and/or with locked nucleic acids that enhance the thermal stability of duplexes. One skilled in the art will recognize that hybridization stringency is a determinant in the degree of match or mismatch in the duplex formed by hybridization.

As used herein, "moiety" refers to one of two or more parts into which something may be divided, such as, for example, the various parts of a tether, a molecule or a probe.

A "polymerase" is an enzyme generally for joining 3'-OH 5'-triphosphate nucleotides, oligomers, and their analogs. Further, "polymerase" in this application is meant to include DNA polymerases of all families, RNA polymerases, and reverse transcriptases.

The term "primer" refers to an oligonucleotide, whether occurring naturally as in a purified restriction digest or produced synthetically, which is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, "degeneracy" or "degenerate" refers to certain equivalencies with respect to the standard genetic code of four nucleotide bases A, C, G, and T. In some contexts, a "degenerate code" is one in which one symbol, character, color, etc. refers to more than one of the bases A, C, G, and T (or U). A degenerate two-base code is one in which the set of symbols representing a nucleic acid sequence has two elements and one element refers to either and/or both of two bases and the second element refers to either and/or both of the other two bases (that is, there is no overlap between the set of two bases denoted by the first element and the set of two bases denoted by the second element). Examples of degenerate codes are the purine/pyrimidine code in which R refers to A or G and Y refers to C or T; the keto base/amino base code in which K refers to G or T and M refers to A or C; and the strong/weak code in which S refers to C or G and W refers to A or T.

In some contexts, "degenerate" refers to the base-pairing behavior of a nucleotide base or nucleotide base analogue. Degenerate base pairing refers to a situation in which one nucleotide or nucleotide analogue can base pair with more than one partner. In some contexts, a "degenerate base pairing rule" describes or defines the set of base pairing partners with which a nucleotide or a nucleotide analogue forms base pairs. For example, a degenerate base pairing rule may describe a nucleotide or nucleotide analogue that base pairs with both A and G, both C and T, both A and C, both G and T, both G and C, and/or both A and T.

Embodiments of the Technology

The technology relates generally to methods, compositions, systems, and kits for DNA sequencing using a two-base degenerate code in, for example, a sequencing-by-synthesis approach. Although the disclosure herein refers to certain illustrated embodiments, it is to be understood that these embodiments are presented by way of example and not by way of limitation.

1. Methods

Some embodiments of the technology provide for methods of DNA sequencing using a degenerate two-base code to identify the bases in the sequence. The technology encompasses various embodiments of degenerate two-base sequencing schemes that identify bases by traits shared by pairs of the four bases A, C, G, and T (alternatively, U). For instance, in some embodiments, the methods rely on differentiating pyrimidine bases (C and T) from purine bases (A and G), producing a sequence denoting pyrimidines with Y and purines with R. In some embodiments, the methods rely on differentiating keto bases (G and T) from amino bases (A and C), producing a sequence denoting keto bases with K and amino bases with M. In some embodiments, the methods rely on differentiating bases that form stronger base pairs (G and C) from those that form weaker base pairs (A and T), producing a sequence denoting bases that form stronger base pairs with S and bases that form weaker base pairs with W. It is to be understood that the standard designations associated with the degenerate base codes R, Y, K, M, S and W are not intended to limit the technology to producing sequences represented only by these particular letters or codes. The technology encompasses methods that use a degenerate two-base code regardless of the notation used to communicate the sequence.

The technology contemplates any sequencing method by which these nucleotide pairs are differentiated from each other, e.g., by physical and/or chemical characteristics such as size, charge, conductivity, inherent fluorescent characteristics, mass, dipole moment, shape, structure, reactivity, etc., and/or by interrogating each nucleotide in the target sequence with some other molecule, such as by monitoring the base pairing of each nucleotide with tagged (e.g., labeled) nucleotides, tagged modified nucleotides, tagged nucleotide analogues, etc.

In some embodiments, an ensemble based sequencing method is used and in some embodiments a single molecule based sequencing method is used. In some embodiments, a sequencing reaction is halted after the incorporation of each nucleotide and in some embodiments synthesis is monitored in real time without the need for interrupting the reaction to identify bases. In some embodiments, molecules of a nucleic acid are interrogated directly without using a sequencing reaction to identify the bases. With respect to sequencing-by-synthesis methods and schemes that find use, e.g., as appropriately adapted to the methods provided herein, Morozova and Marra provide a review of some such technologies in *Genomics* 92: 255 (2008); additional discussions are found in Mardis, *Annu. Rev. Genomics Hum. Genet.* (2008) 9:387-402 and in Fuller, et al. (2009) *Nat. Biotechnol.* 27: 1013.

In an ensemble based method, tens of thousands to tens of millions of nominally identical strands are localized at a given location (e.g., on a bead or other solid surface or substrate) to be read in a process comprising iterations of washing and scanning. In conventional use, this process involves adding reagents (e.g., labeled nucleotides), incorporating nucleotides into DNA strands (e.g., by a polymerase), stopping the incorporation reaction, removing or inactivating excess reagent, identifying the incorporated bases (e.g., optical detection of fluorescence emission from a nucleotide label; detecting a change in pH or voltage), and, in some embodiments, treating the newly incorporated bases to prepare the DNA templates for the next base addition. These steps continue until the process sequences the entire target nucleotide or fails to produce satisfactory sequence results.

In general, ensemble based methods depend on stopping the sequencing reaction after each base incorporation to keep the population of synthesized molecules in phase so that the detection (e.g., imaging) accurately reports the base incorporated by the synthesis at each step. Phasing is maintained in various embodiments by adding one base at a time (see, e.g., Margulies, M. et al. "Genome sequencing in microfabricated high-density picoliter reactors", *Nature* 437: 376-380 (2005); Harris, T. D. et al. "Single-molecule DNA sequencing of a viral genome", *Science* 320: 106-109 (2008)) or by using reversibly blocked nucleotides that allow only one base incorporation during each iteration of the cycle.

For example, some embodiments comprise use of particular technologies for parallel sequencing of partitioned amplicons (PCT Publication No: WO 2006/084132); parallel oligonucleotide extension (See, e.g., U.S. Pat. No. 5,750,341; U.S. Pat. No. 6,306,597); polony sequencing (Mitra et al. (2003) *Analytical Biochemistry* 320: 55-65; Shendure et al. (2005) *Science* 309: 1728-1732; U.S. Pat. No. 6,432,360, U.S. Pat. No. 6,485,944, U.S. Pat. No. 6,511,803); the Solexa single base addition technology (see, e.g., Bennett et al. (2005), *Pharmacogenomics* 6: 373-382; U.S. Pat. No. 6,787,308; U.S. Pat. No. 6,833,246; herein incorporated by reference in their entireties), the Lynx massively parallel signature sequencing technology (Brenner et al. (2000). *Nat. Biotechnol.* 18: 630-634; U.S. Pat. No. 5,695,934; U.S. Pat. No. 5,714,330), and the Adessi PCR colony technology (Adessi et al. (2000). *Nucleic AcidRes.* 28: E87; WO 00/018957).

In particular embodiments, extension is momentarily blocked following each base addition by using modified nucleotides (e.g., nucleotide reversible terminators as described in, e.g., WO 2004/018497; U.S. Pat. Appl. Pub. No. 2007/0166705; Bentley, D. R. et al. "Accurate whole human genome sequencing using reversible terminator chemistry", *Nature* 456: 53-59 (2008); Turcatti, G. et al. "A new class of cleavable fluorescent nucleotides: synthesis and optimization as reversible terminators for DNA sequencing by synthesis", *Nucleic Acids Res.* 36: e25 (2008); Guo, J. et al. "Four-color DNA sequencing with 3'-O-modified nucleotide reversible terminators and chemically cleavable fluorescent dideoxynucleotides", *Proc. Natl Acad Sci USA* 105: 9145-9150 (2008); Ju, J. et al. "Four-color DNA sequencing by synthesis using cleavable fluorescent nucleotide reversible terminators", *Proc. Natl. Acad Sci USA* 103: 19635-19640 (2006); Seo, T. S. et al. "Four-color DNA sequencing by synthesis on a chip using photocleavable fluorescent nucleotides", *Proc. Natl. Acad Sci USA* 102: 5926-5931 (2005); Wu, W. et al. "Termination of DNA synthesis by N6-alkylated, not 3'-O-alkylated, photocleavable 2'-deoxyadenosine triphosphates", *Nucleic Acids Res.* 35: 6339-6349 (2007)) or by omitting reaction components such as divalent metal ions (see, e.g., WO 2005/123957; U.S. Pat. Appl. Pub. No. 20060051807).

Embodiments of the present technology relate to methods of ensemble sequencing in which 1, 2, 3, or 4 nucleotides is/are added at each sequencing round. In some embodiments, two labels are used to label two pairs of nucleotides. That is, two nucleotides are labeled with a first label (e.g., a first fluorescent moiety) and the other two nucleotides are labeled with a second label (e.g., a second fluorescent moiety). For instance, in some embodiments, the purines A and G are labeled with a first label and the pyrimidines are labeled with a second label; in some embodiments, the keto bases G and T are labeled with a first label and the amino bases A and C are labeled with a second label; in some embodiments, the strongly hydrogen bonding bases C and G are labeled with a first label and the weakly hydrogen bonding bases A and T are labeled with a second label. In embodiments in which more than one type of nucleotide are added at each round, the nucleotides are reversibly blocked, e.g., with a reversible terminator, to halt the synthesis after each incorporation of one of the added nucleotides.

In some embodiments in which one nucleotide is added at a time, two differentially labeled nucleotide analogues are used wherein each nucleotide analogue base pairs with two nucleotides according to a degenerate base pairing rule. In particular, the two nucleotides with which the first nucleotide analogue base pairs are different than the two nucleotides with which the second nucleotide analogue base pairs (without overlap of the two sets). For example, in some embodiments, two nucleotide analogues X and Y are used in an ensemble sequencing by synthesis reaction wherein X hydrogen bonds with a purine and Y hydrogen bonds with a pyrimidine. Sequentially adding X and Y to the reaction (e.g., adding X, then adding Y, then adding X, then adding Y, etc., optionally with a wash step after each addition) generates a sequence of purines (e.g., R=A or G) and pyrimidines (e.g., Y=C or T) of the template (target) nucleic acid. Similar embodiments comprise adding two nucleotide analogues that hydrogen bond according to a degenerate rule in which one nucleotide analogue binds to an amino base (e.g., M=A or C) and the other nucleotide analogue binds to a keto base (e.g., K=G or T). Similarly, embodiments comprise adding two nucleotide analogues that hydrogen bond according to a degenerate rule in which one nucleotide analogue binds to a strong hydrogen bonding base (e.g., S=C or G) and the other nucleotide analogue binds to a weak hydrogen binding base (e.g., W=A or T).

If the sequence being determined is unknown, the nucleotides or nucleotide analogues added are usually applied in a chosen order that is then repeated throughout the analysis. If, however, the sequence being determined is known and is being re-sequenced, for example, to determine if small differences are present in the sequence relative to the known sequence, the sequencing determination process may be made quicker by adding the nucleotides at each step in the appropriate order, e.g., chosen according to the known sequence. Differences from the given sequence are thus detected by the lack of incorporation of certain nucleotides at particular stages of primer extension.

In addition, embodiments of single molecule based sequencing involve methods comprising different fundamental technologies, e.g., monitoring a polymerase molecule as it incorporates nucleotides into a synthesized DNA strand; passing a nucleic acid molecule (or its nucleotide monomers) through or over or near a probe structure (e.g., through a tube or a pore) and monitoring the interactions of each nucleotide base with the probe structure (e.g., a change in voltage, a change in current, a change in optical properties); observing the synthesis of a DNA molecule directly using microscopy (e.g., STM, TEM); or observing a molecule of a nucleic acid directly and identifying the individual bases by direct observation.

Embodiments of the methods provided herein comprise single molecule sequencing based on a two-base degenerate code. For example, in some embodiments a molecule of DNA is observed directly and the sequence of purine and pyrimidine bases (or, alternatively, the keto and amino or the strongly and weakly hydrogen bonding bases) is discerned based on physical characteristics such as the shape, size, and/or mass of each base. As another example, in some embodiments a molecule of a nucleic acid is threaded through a nanopore and the sequence of keto and amino bases (or, alternatively, the purine and pyrimidine bases or the strongly and weakly hydrogen bonding bases) is discerned by the different changes in current and/or potential across the nanopore induced by keto and amino bases.

Some embodiments of single molecule sequencing in which synthesis is monitored (e.g., by direct observation, by detecting changes in fluorescence, etc.) use two labels to label pairs of nucleotides as described above for the ensemble methods. In particular, these embodiments comprise using a first pair of nucleotides labeled with a first label (e.g., a first fluorescent moiety) and a second pair of nucleotides labeled with a second label (e.g., a second fluorescent moiety) and/or a pair of labeled nucleotide analogues wherein each nucleotide analogue base pairs with two nucleotides according to a degenerate base pairing rule (e.g., as discussed above for the ensemble embodiments).

During each cycle, the detection of an output signal appropriate for the base added in the previous step indicates a successful incorporation of that base and thus identifies the base incorporated at that step. Detection may be by conventional modes. For example, if the label is a fluorescent moiety, then detection of an incorporated base may be carried out by using a confocal scanning microscope to scan the collection of clusters (e.g., attached to a surface) with a laser to image the fluorescent moieties bound directly to the incorporated bases. Alternatively, a sensitive 2D detector, such as a charge coupled detector (CCD), can be used to visualize the signals generated. However, other techniques such as scanning near-field optical microscopy (SNOM) are available and may be used when imaging dense arrays. For example, using SNOM, individual polynucleotides may be distinguished when separated by a distance of less than 100 nm, e.g. 10 nm to 10 fm. For a description of scanning near-field optical microscopy, see Moyer et al., *Laser Focus World* (1993) 29:10. Suitable apparatuses used for imaging polynucleotide arrays are known and the technical set-up is apparent to the skilled person. The detection is preferably used in combination with an analysis system to determine the number and nature of the nucleotide bases incorporated for each step of synthesis. This analysis, which may be carried out immediately after each synthesis step, or later using recorded data, allows the sequence of the nucleic acid template to be determined.

Examples of sequencing technologies for which the present technology is appropriate and/or for which the present technology is adapted are discussed below. In some embodiments, pyrosequencing methods are used. In pyrosequencing (Voelkerding et al., *Clinical Chem.*, 55: 641-658, 2009; MacLean et al., *Nature Rev. Microbiol.*, 7' 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol*, 7.287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55.641-658, 2009; MacLean et al., *Nature Rev. Microbiol.*, 7'287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (see, e.g., Astier et al. (2006), *J Am. Chem. Soc.* 128: 1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.*, 55: 641-658, 2009; MacLean et al., *Nature Rev. Microbiol.*, 7:287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mbp generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., *Clinical Chem.*, 55:641-658, 2009; MacLean et al., *Nature Rev. Microbiol.*, 7:287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

With this single molecule real time (SMRT) DNA sequencing technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes, compositions, and systems for sequencing that may be adapted for use with the invention are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flowcell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analogue incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" *PNAS* 105(4): 1176-81, all of which are herein incorporated by reference in their entireties.

2. Compositions

The technology provides compositions comprising one or more bases, e.g., for use in nucleic acid sequencing using a degenerate two-base code. In some embodiments, bases are labeled in pairs, e.g., two of the four nucleotide bases are labeled with a first label and the remaining (other) two of the four nucleotide bases are labeled with a second label such that a base of the first pair is differentiated from a base in the second pair, but the bases within each pair are not differentiated from each other with respect to the label attached to them.

The technology encompasses various embodiments of compositions comprising labeled bases and/or base analogues. For example, in some embodiments, compositions comprise one or more bases that are labeled to differentiate pyrimidine bases (C and T) from purine bases (A and G), e.g., for use in a method for producing a sequence denoting the sequence of pyrimidines (e.g., "Y") and purines (e.g., with "R"). In some embodiments, bases are labeled to differentiate keto bases (G and T) from amino bases (A and C), e.g., for use in a method for producing a sequence denoting the sequence of keto bases (e.g., "K") and amino bases (e.g., "M"). In some embodiments, bases are labeled to differentiate bases that form stronger base pairs (G and C) from those that form weaker base pairs (A and T), e.g., for use in a method for producing a sequence denoting the sequence of bases that form stronger base pairs (e.g., "S") and bases that form weaker base pairs (e.g., "W").

In some embodiments, compositions comprise one or more base analogues that base pair with the four nucleotide bases according to a degenerate base pairing rule; that is, each nucleotide analogue base pairs with two nucleotides according to a degenerate base pairing rule. In particular, the two nucleotides with which the first nucleotide analogue base pairs are different (without overlap) than the two nucleotides with which the second nucleotide analogue base pairs. For example, in some embodiments, compositions comprise one or two nucleotide analogues X and Y wherein X base pairs with a purine and Y base pairs with a pyrimidine. Similar embodiments comprise compositions of one or two nucleotide analogues that base pair according to a degenerate rule in which one nucleotide analogue pairs with an amino base (e.g., M=A or C) and the other nucleotide analogue pairs with a keto base (e.g., K=G or T). Similarly, embodiments comprise compositions of one or two nucleotide analogues base pair according to a degenerate rule in which one nucleotide analogue pairs with a strong hydrogen bonding base (e.g., S=C or G) and the other nucleotide analogue pairs with a weak hydrogen binding base (e.g., W=A or T).

Base pair analogues that acts as a degenerate purine and pyrimidine nucleotide (e.g., that base pair according to a degenerate base pairing rule in which the nucleotide binds recognizes, and base pairs with, both A and G or both C and T) are described, for example, in Abraham, et al., "Nucleobase analogs for degenerate hybridization devised through conformational pairing analysis" (2007), *Biotechniques* 43: 617. See also Linet al., "Synthesis of oligodeoxyribonucleotides containing degenerate bases and their use as primers in the polymerase chain reaction" (1992), *Nucleic Acids Res.* 19: 5149. Additional examples are 8-hydroxyguanine, 2-hydroxyadenine, 6-O-methylguanine, and xanthine, which base pair with C and A (e.g., M); T and A (W); T and C (e.g., Y); and T and C (e.g., Y), respectively, and thus act as bases that can be denoted as K, S, R, and R, respectively. Nonstandard bases may be incorporated by polymerases, e.g., as described in International Patent Application WO 2009/154733.

According to some embodiments of the technology, bases are labeled with a moiety that results in the production of a detectable signal upon the incorporation of the base into the DNA strand being synthesized. In some embodiments, the moiety produces a signal (e.g., fluorescence) prior to incorporation and/or after incorporation. In some embodiments, the moiety is linked in such a way that is appropriate for removing the moiety after incorporation or after imaging. The labeling moiety is, in some embodiments, a fluorescent organic dye derivatized for attachment to the base directly or via a linker. Practical guidance is available in the literature that provides a list of fluorescent and chromogenic molecules and their relevant optical properties (see, for example, Berlman, *Handbook of Fluorescence Spectra of Aromatic Molecules,* 2nd edition (Academic Press, New York, 1971); Griffiths, *Colour and Constitution of Organic Molecules* (Academic Press, New York, 1976); Bishop, Ed., Indicators (Pergamon Press, Oxford, 1972); Haugland, *Handbook of Fluorescent Probes and Research Chemicals* (Molecular Probes, Eugene, 1992); Pringsheim, *Fluorescence and Phosphorescence* (Interscience Publishers, New York, 1949); and the like.

Further, there is guidance in the literature for derivatizing fluorescent molecules for covalent attachment via common reactive groups that can be added to a nucleotide, as exemplified by Haugland (supra); Ullman et al, U.S. Pat. No. 3,996,345; Khanna et al, U.S. Pat. No. 4,351,760. There are many linking moieties and methodologies for attaching fluorescent labels or quencher moieties to nucleotides, as exemplified by the following references: Eckstein, editor, *Oligonucleotides and Analogues: A Practical Approach* (IRL Press, Oxford, 1991); Zuckerman et al. (1987), *Nucleic Acids Research* 15: 5305-5321; Sharma et al. (1991), *Nucleic Acids Research* 19: 3019; Giusti et al., PCR Methods and Applications 2: 223-227 (1993); Fung et al., U.S. Pat. No. 4,757,141; Stabinsky, U.S. Pat. No. 4,739,044; Agrawal et al. (1990), *Tetrahedron Letters* 31: 1543-1546; Sproat et al. (1987), *Nucleic Acids Research* 15: 4837; Nelson et al. (1989), *Nucleic Acids Research* 17: 7187-7194; and the like. A number of DNA fluorescence-based sequencing methodologies are known in the art (see, e.g., Birren et al., *Genome Analysis: Analyzing DNA,* (Cold Spring Harbor, N.Y.)).

Embodiments of the technology comprise compositions comprising a target nucleic acid template. In some embodiments, the composition comprises a primer, e.g., in some embodiments that is bound to the target nucleic acid template.

The target nucleic acid is not critical and can come from a variety of standard sources. It can be mRNA, ribosomal RNA, genomic DNA, or cDNA. When the target is from a biological source, procedures are known for extracting nucleic acid and optionally amplifying it to a concentration convenient for genotyping or sequence work. Nucleic acid can be obtained from any living cell of a person, animal, or plant (and in many cases from dead cells or other matter of biological origin). Humans, pathogenic microbes, and viruses are particularly interesting sources. Nucleic acid amplification methods are also known. Preferably, the amplification is carried out by polymerase chain reaction (PCR) (U.S. Pat. Nos. 4,683,202; 4,683,195; and U.S. Pat. No. 4,889,818; Gyllenstein et al (1988) *Proc. Natl Acad Sci USA* 85: 7652-7656; Ochman et al. (1988) *Genetics* 120: 621-623; Loh et al (1989) *Science* 243: 217-220; Innis et al (1990) PCR Protocols (Academic Press, San Diego, Calif.). Other amplification methods known in the art can be used, including but not limited to ligase chain reaction (see, e.g., EP 320308), use of Q-beta replicase, or methods listed in Kricka et al., 1995, *Molecular* Probing, *Blotting, and Sequencing* (*Academic Press*, New York), especially Chap. 1 and Table IX.

The technology provided herein relates to the use of a polymerase in a sequencing reaction. In general, the polymerases that find use in the technology tolerate labels in various positions, e.g., on the nucleobase, on the gamma-phosphate, on the 3' hydroxyl, etc. For instance, polymerases that find use in the technology include, but are not limited to, DNA-dependent DNA polymerases, DNA-dependent RNA polymerases, RNA-dependent DNA polymerases, RNA-dependent RNA polymerases, T7 DNA polymerase, T3 DNA polymerase, T4 DNA polymerase, T7 RNA polymerase, T3 RNA polymerase, SP6 RNA polymerase, DNA polymerase 1, Klenow fragment, *Thermophilus aquaticus* DNA polymerase, Tth DNA polymerase, Vent DNA polymerase (New England Biolabs), Deep Vent DNA polymerase (New England Biolabs), BstDNA Polymerase Large Fragment, Stoeffel Fragment, 9° N DNA Polymerase, Pfu DNA Polymerase, Tfl DNA Polymerase, RepliPHI Phi29 Polymerase, TliDNA polymerase, eukaryotic DNA polymerase beta, telomerase, Therminator polymerase (New England Biolabs), KOD HiFi. DNA polymerase (Novagen), KOD 1 DNA polymerase, Q-beta replicase, terminal transferase, AMV reverse transcriptase, M-MLV reverse transcriptase, Phi6 reverse transcriptase, HIV-1 reverse transcriptase, novel polymerases discovered by bioprospecting, and polymerases cited in U.S. Pat. Appl. Pub. No. 2007/0048748 and in U.S. Pat. Nos. 6,329,178; 6,602,695; and 6,395,524. These polymerases include wild-type, mutant isoforms, and genetically engineered variants. In some embodiments, an exonuclease-defective polymerases is used. In some embodiments (e.g., a reversible terminator technology), a polymerase having an exonuclease activity is used for some or all steps.

The primers (for syntheses by DNA polymerase) or promoters (for syntheses by RNA polymerase) are typically synthetically made using conventional nucleic acid synthesis technology, e.g., using an automated DNA synthesizer and standard chemistries, such as phosphoramidite chemistry, e.g., as disclosed in the following references: Beaucage and Iyer, *Tetrahedron* 48: 2223-211 (1992); U.S. Pat. No. 4,980,460; U.S. Pat. No. 4,725,677; U.S. Pat. Nos. 4,415,732; 4,458,066; and 4,973,679; and the like. Alternative chemistries, e.g., resulting in non-natural backbone groups, such as phosphorothioate, phosphoramidate, and the like, may also be employed provided that the resulting oligonucleotides are compatible with the polymerase. They can be ordered commercially from a variety of companies that specialize in custom oligonucleotides such as Operon, IDT, Dharmacon, etc.

Primers in combination with polymerases are used to sequence target DNA. Primer length is selected to provide for hybridization to complementary template DNA. The primers are generally at least 10 nt in length, usually at least between 15 and 30 nt in length. Primers are designed to hybridize to known internal sites on the subject target DNA. Alternatively, the primers can bind to synthetic oligonucleotide adaptors joined to the ends of target DNA by a ligase. Similarly, where promoters are used, they can be internal to the target DNA or ligated as adaptors to the ends.

The reaction mixture for the sequencing comprises an aqueous buffer medium that is optimized for the particular polymerase chosen. In general, the buffer typically includes a source of monovalent ions, a source of divalent cations, and a buffering agent. Any convenient source of monovalent ions, such as potassium chloride, potassium acetate, potassium acetate, potassium glutamate, ammonium chloride, ammonium sulfate, and the like may be employed.

The divalent cation may be magnesium, managanese, zinc, and the like, where the cation will typically be magnesium. Any convenient source of magnesium cation may be employed, including $MgCl_2$, magnesium acetate, and the like. The amount of Mg ion present in the buffer may range from 0.5 to 20 mM, but will preferably range from about 1 to 12 mM, more preferably from 2 to 10 mM, and will ideally be about 5 mM.

Representative buffering agents or salts that may be present in compositions according to the technology described (e.g., in a composition comprising a labeled nucleotide or in a SBS reaction) include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5. Other agents which may be present in the buffer medium include chelating agents, such as EDTA, EGTA, and the like.

In some embodiments, the label (e.g., fluorescent moiety) is attached to the nucleotide base and in some embodiments the label is attached to the phosphate chain (e.g., in methods such as Pacific Biosciences SMRT sequencing).

3. Data Analysis

Some embodiments comprise a computer system upon which embodiments of the present teachings may be implemented. In various embodiments, a computer system includes a bus or other communication mechanism for communicating information and a processor coupled with the bus for processing information. In various embodiments, the computer system includes a memory, which can be a random access memory (RAM) or other dynamic storage device, coupled to the bus for identifying bases (e.g., making "base calls"), and instructions to be executed by the processor. Memory also can be used for storing temporary variables or other intermediate information during execution of instructions to be executed by the processor. In various embodiments, the computer system can further include a read only memory (ROM) or other static storage device coupled to the bus for storing static information and instructions for the processor. A storage device, such as a magnetic disk or optical disk, can be provided and coupled to the bus for storing information and instructions.

In various embodiments, the computer system is coupled via the bus to a display, such as a cathode ray tube (CRT) or a liquid crystal display (LCD), for displaying information to a computer user. An input device, including alphanumeric and other keys, can be coupled to the bus for communicating information and command selections to the processor. Another type of user input device is a cursor control, such as a mouse, a trackball, or cursor direction keys for communicating direction information and command selections to the processor and for controlling cursor movement on the display. This input device typically has two degrees of freedom in two axes, a first axis (e.g., x) and a second axis (e.g., y), that allows the device to specify positions in a plane.

A computer system can perform embodiments of the present technology. Consistent with certain implementations of the present teachings, results can be provided by the computer system in response to the processor executing one or more sequences of one or more instructions contained in the memory. Such instructions can be read into the memory from another computer-readable medium, such as a storage device. Execution of the sequences of instructions contained in the memory can cause the processor to perform the methods described herein. Alternatively, hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to the processor for execution. Such a medium can take many forms, including but not limited to, non-volatile media, volatile media, and transmission media. Examples of non-volatile media can include, but are not limited to, optical or magnetic disks. Examples of volatile media can include, but are not limited to, dynamic and flash memory. Examples of transmission media can include, but are not limited to, coaxial cables, copper wire, and fiber optics, including the wires that comprise the bus.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to the processor for execution. For example, the instructions can initially be carried on the magnetic disk of a remote computer. The remote computer can load the instructions into its dynamic memory and send the instructions over a network connection (e.g., a LAN, a WAN, the internet, a telephone line). A local computer system can receive the data and transmit it to the bus. The bus can carry the data to the memory, from which the processor retrieves and executes the instructions. The instructions received by the memory may optionally be stored on a storage device either before or after execution by the processor.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In accordance with such a computer system, some embodiments of the technology provided herein further comprise functionalities for collecting, storing, and/or analyzing data (e.g., nucleotide sequence data). For example, some embodiments contemplate a system that comprises a processor, a memory, and/or a database for, e.g., storing and executing instructions, analyzing imaging data from a sequencing reaction, performing calculations using the data, transforming the data, and storing the data. It some embodiments, a base-calling algorithm assigns a sequence of bases to the data and associates quality scores to base calls based on a statistical model. In some embodiments, the system is configured to assemble a sequence from multiple sub-sequences, in some instances accounting for overlap and calculating a consensus sequence. In some embodiments, a sequence is aligned to a reference sequence or to a scaffold.

In some embodiments, two or more degenerate sequences of the same nucleic acid are analyzed in combination to provide a "merged" sequence in conventional four-base notation. For example, a first two-base degenerate sequence of RYRY and a second two-base degenerate sequence MMKK for the same sequence indicates that the first position is an amino purine base, the second position is an amino pyrimidine base, the fourth position is a keto purine base, and the fourth position is a keto pyrimidine base, thus resulting in the conventional four-base sequence ACGT for the nucleic acid.

Many diagnostics involve determining the presence of, or a nucleotide sequence of, one or more nucleic acids. Thus, in some embodiments, an equation comprising variables representing the presence or sequence properties of multiple nucleic acids produces a value that finds use in making a diagnosis or assessing the presence or qualities of a nucleic acid. As such, in some embodiments this value is presented by a device, e.g., by an indicator related to the result (e.g., an LED, an icon on an LCD, a sound, or the like). In some embodiments, a device stores the value, transmits the value, or uses the value for additional calculations.

Moreover, in some embodiments a processor is configured to control the sequencing reactions and collect the data (e.g., images). In some embodiments, the processor is used to initiate and/or terminate each round of sequencing and data collection relating to a sequencing reaction. Some embodiments comprise a processor configured to analyze the data and discern the sequence of the target nucleic acid and/or of its complement.

In some embodiments, a device that comprises a user interface (e.g., a keyboard, buttons, dials, switches, and the like) for receiving user input is used by the processor to direct a measurement. In some embodiments, the device further comprises a data output for transmitting (e.g., by a wired or wireless connection) data to an external destination, e.g., a computer, a display, a network, and/or an external storage medium.

In some embodiments, the technology finds use in assaying the presence of one or more nucleic acids and/or providing the sequence of one or more nucleic acids. Accordingly, the technology provided herein finds use in the medical, clinical, and emergency medical fields. In some embodiments a device is used to assay biological samples. In such an assay, the biological sample comprises a nucleic acid and sequencing the nucleic acid is indicative of a state or a property of the sample and, in some embodiments, the subject from which the sample was taken. Some relevant samples include, but are not limited to, whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate, a tissue homogenate, a cell homogenate, or the like.

The sequence of output signals provides the sequence of the synthesized DNA and, by the rules of base complementarity, also thus provides the sequence of the template strand.

Apparatuses

A further aspect of the invention provides an apparatus for carrying out the methods or for preparing the compositions of the technology. Such an apparatus might comprise, for example, a plurality of nucleic acid templates and primers bound, preferably covalently, to a solid support, together with a nucleic acid polymerase, a plurality of nucleotides or nucleotide analogues such as those described above, and a functionality for controlling temperature and/or nucleotide additions. Preferably the apparatus also comprises a detecting functionality for detecting and distinguishing signals from individual nucleic acid clusters. Such a detecting functionality might comprise a charge-coupled device operatively connected to a magnifying device such as a microscope. Preferably any apparatuses of the invention are provided in an automated form, e.g., under the control of a program of steps and decisions, e.g., as implemented in computer software.

Some embodiments of such an apparatus include a fluidic delivery and control unit; a sample processing unit; a signal detection unit; and a data acquisition, analysis, and control unit. Various embodiments of the apparatus can provide for automated sequencing that can be used to gather sequence information from a plurality of sequences in parallel, e.g., substantially simultaneously.

In various embodiments, the fluidics delivery and control unit includes a reagent delivery system. The reagent delivery system can include a reagent reservoir for the storage of various reagents (e.g., compositions of nucleotides or nucleotide analogues according to the technology). The reagents can include RNA-based primers, forward/reverse DNA primers, oligonucleotide mixtures for ligation sequencing, nucleotide mixtures for sequencing-by-synthesis, buffers, wash reagents, blocking reagent, stripping reagents, and the like. Additionally, the reagent delivery system can include a pipetting system or a continuous flow system that connects the sample processing unit with the reagent reservoir.

In various embodiments, the sample processing unit can include a sample chamber, such as flow cell, a substrate, a micro-array, a multi-well tray, or the like. The sample processing unit can include multiple lanes, multiple channels, multiple wells, or other modes of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit can include an imaging or detection sensor. The signal detection unit can include an excitation system to cause a probe, such as a fluorescent dye, to emit a signal. The excitation system can include an illumination source, such as arc lamp, a laser, a light emitting diode (LED), or the like. In particular embodiments, the signal detection unit can include optics for the transmission of light from an illumination source to the sample or from the sample to the imaging or detection sensor. Alternatively, the signal detection unit may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal.

In various embodiments, a data acquisition analysis and control unit can monitor various system parameters. The system parameters can include the temperature of various portions of the instrument, such as a sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of such an instrument can be used to practice a variety of sequencing methods including ligation-based methods, sequencing by synthesis, single molecule methods, and other sequencing techniques. Ligation sequencing can include single ligation techniques, or change ligation techniques where multiple ligations are performed in sequence on a single primary. Sequencing by synthesis can include the incorporation of dye labeled nucleotides, chain termination, or the like. Single molecule techniques can include staggered sequencing, where the sequencing reactions are paused to determine the identity of the incorporated nucleotide.

In various embodiments, the sequencing instrument can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument can obtain the sequence information from a group of substantially identical nucleic acid molecules.

In various embodiments, the sequencing instrument can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Some embodiments comprise a system for reconstructing a nucleic acid sequence, e.g., a two-base generate base sequence or a "merged" four-base sequence, in accordance with the various embodiments provided herein. The system can include a nucleic acid sequencer, a sample sequence data storage, a reference sequence data storage, and an analytics computing device/server/node. In various embodiments, the analytics computing device/server/node can be a workstation, a mainframe computer, a personal computer, a mobile device, etc.

The nucleic acid sequencer can be configured to analyze (e.g., interrogate) a nucleic acid fragment (e.g., single fragment, mate-pair fragment, paired-end fragment, etc.) utilizing all appropriate varieties of techniques, platforms, or technologies to obtain nucleic acid sequence information, e.g., using an ensemble sequencing by synthesis. In various embodiments, the nucleic acid sequencer can be in communications with the sample sequence data storage either directly via a data cable (e.g., a serial cable, a direct cable connection, etc.) or bus linkage or, alternatively, through a network connection (e.g., Internet, LAN, WAN, VPN, etc.). In various embodiments, the network connection can be a "hardwired" physical connection. For example, the nucleic acid sequencer can be communicatively connected (via Category 5 (CAT5), fiber optic, or equivalent cabling) to a data server that can be communicatively connected (via CAT5, fiber optic, or equivalent cabling) through the internet and to the sample sequence data storage. In various embodiments, the network connection can be a wireless network connection (e.g., Wi-Fi, WLAN, etc.), for example, utilizing an 802.11b/g or equivalent transmission format. In practice, the network connection utilized is dependent upon the particular requirements of the system. In various embodiments, the sample sequence data storage can be an integrated part of the nucleic acid sequencer.

In various embodiments, the sample sequence data storage can be any database storage device, system, or implementation (e.g., data storage partition, etc.) that is configured to organize and store nucleic acid sequence read data generated by the nucleic acid sequencer such that the data can be searched and retrieved manually (e.g., by a database administrator/client operator) or automatically by way of a computer program/application/software script. In various embodiments, the reference data storage can be any database device, storage system, or implementation (e.g., data storage partition, etc.) that is configured to organize and store reference sequences (e.g., whole/partial genome, whole/partial exome, etc.) such that the data can be searched and retrieved manually (e.g., by a database administrator/client operator) or automatically by way of a computer program/application/software script. In various embodiments, the sample nucleic acid sequencing read data can be stored on the sample sequence data storage and/or the reference data storage in a variety of different data file types/formats, including, but not limited to: *.fasta, *.csfasta, *seq.txt, *qseq.txt, *.fastq, *.sff, *prb.txt, *.sms, *srs and/or *.qv.

In various embodiments, the sample sequence data storage and the reference data storage are independent stand-alone devices/systems or implemented on different devices. In various embodiments, the sample sequence data storage and the reference data storage are implemented on the same device/system. In various embodiments, the sample sequence data storage and/or the reference data storage can be implemented on the analytics computing device/server/node.

The analytics computing device/server/node can be in communications with the sample sequence data storage and the reference data storage either directly via a data cable (e.g., serial cable, direct cable connection, etc.) or bus linkage or, alternatively, through a network connection (e.g., Internet, LAN, WAN, VPN, etc.). In various embodiments, the analytics computing device/server/node can host a reference mapping engine, a de novo mapping module, and/or a tertiary analysis engine. In various embodiments, the reference mapping engine can be configured to obtain sample nucleic acid sequence reads from the sample data storage and map them against one or more reference sequences obtained from the reference data storage to assemble the reads into a sequence that is similar but not necessarily identical to the reference sequence using all varieties of reference mapping/alignment techniques and methods. The reassembled sequence can then be further analyzed by one or more optional tertiary analysis engines to identify differences in the genetic makeup (genotype), gene expression, or epigenetic status of individuals that can result in large differences in physical characteristics (phenotype). For example, in various embodiments, the tertiary analysis engine can be configured to identify various genomic variants (in the assembled sequence) due to mutations, recombination/crossover, or genetic drift. Examples of types of genomic variants include, but are not limited to: single nucleotide polymorphisms (SNPs), copy number variations (CNVs), insertions/deletions (Indels), inversions, etc.

The optional de novo mapping module can be configured to assemble sample nucleic acid sequence reads from the sample data storage into new and previously unknown sequences.

It should be understood, however, that the various engines and modules hosted on the analytics computing device/server/node can be combined or collapsed into a single engine or module, depending on the requirements of the particular application or system architecture. Moreover, in various embodiments, the analytics computing device/server/node can host additional engines or modules as needed by the particular application or system architecture.

In various embodiments, the mapping and/or tertiary analysis engines are configured to process the nucleic acid and/or reference sequence reads in signal ratio space. In various embodiments, the sample nucleic acid sequencing read and referenced sequence data can be supplied to the analytics computing device/server/node in a variety of different input data file types/formats, including, but not limited to: *.fasta, *.csfasta, *seq.txt, *qseq.txt, *.fastq, *.sff, *prb.txt, *.sms, *srs and/or *.qv.

Uses

The technology provides the use of the methods of the technology, or the compositions of the technology, for sequencing and/or re-sequencing nucleic acid molecules for gene expression monitoring, genetic diversity profiling, diagnosis, screening, whole genome sequencing, whole genome polymorphism discovery and scoring, or any other application involving the analysis of nucleic acids where sequence or partial sequence information is relevant.

Kits

A yet further aspect of the invention provides a kit for use in sequencing, re-sequencing, gene expression monitoring, genetic diversity profiling, diagnosis, screening, whole genome sequencing, whole genome polymorphism discovery and scoring, or any other application involving the sequencing of nucleic acids. In some embodiments, kits comprise at least one labeled nucleotide or nucleotide analogue labeled according to the technology described.

EXAMPLES

Example 1—Next Generation DNA Sequencing with Degenerate Nucleotides

During the development of embodiments of the technology, experiments were performed in which a degenerate sequence was determined using a degenerate nucleotide mixture and the degenerate sequence was used to identify a DNA target sequence.

Materials and Methods

A DNA library was constructed from the products of a reverse transcriptase whole genome amplification reaction. The template was the RNA virus, MS2, which is a well described bacteriophage. This library has been previous sequenced using conventional 4-base sequencing (e.g., Ion Torrent sequencing technology). The whole genome amplification product was sequenced with the Ion Torrent Next Generation DNA sequencing technology with and without degenerate bases. For this experiment, adenosine (A) and cytosine (C) bases were kept separate while guanine (G) and thymine (T) bases were mixed together (e.g., degenerate G/T) and the mixture was used in place of both G and T. Other than the mixed G/T bases, standard conditions for sequencing with the Ion Torrent platform were utilized.

Results

The DNA sequencing reactions were successful in generating 64 megabases (64 million bases) of sequence data. The sequence data comprises 573,000 total reads having an average read length of 116 bp. Two randomly chosen experimental reads acquired using embodiments of the technology (FIG. 2, "read 2.1" and FIG. 3, "read 3.1") were used to demonstrate the ability to map the sequences acquired by the experiment to the known MS2 genome (accession number NC_001417.2).

As shown for each read below in FIG. 2 and FIG. 3, the "observed sequence" is the sequence read generated by the Ion Torrent sequencer under standard conditions. As shown for each read below in FIG. 2 and FIG. 3, the "degenerate sequence" was generated under the experimental conditions in which the Gs and Ts were mixed together and used in place of both G and T. The degenerate sequence is shown using the degenerate single letter code of K, which denotes a position in which is found G or T. The Ion Torrent sequencer software called the degenerate Ks as either G or T as the Ion Torrent software and system are not designed to use mixed bases; as such, the results were manually converted to use the degenerate code K. The indicated "homology" denotes the matching of the "degenerate sequence" to the MS2 genome. For read 2.1, alignment of the read to the MS2 genome identified over 180 bases, which corresponds to an accuracy of 94%. For read 3.1, alignment of the read to the MS2 genome identified over 193 bases, which corresponds to an accuracy of 90%.

Analysis of the data indicated that errors were due the sequencer used and not specifically the result of the degenerate (mixed) nucleotides.

In sum, the data collected in this experiment demonstrated that the use of degenerate nucleotides with a next generation sequencing technology correctly identifies a target.

Various modifications and variations of the described compositions, methods, systems, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in related fields are intended to be within the scope of the following claims.

I claim:

1. A method for sequencing a target nucleic acid, the method comprising:
   a) choosing a two-base degenerate code; and
   b) sequencing a two-base degenerate sequence of the target nucleic acid using the two-base degenerate code and a first nucleotide, a second nucleotide, a third nucleotide and a fourth nucleotide wherein the first nucleotide is labeled with a first label and the second nucleotide is labeled with said first label wherein the third nucleotide is labeled with a second label, and the fourth nucleotide is labeled with said second label wherein the first labeled nucleotide and the second labeled nucleotide base pair with a first nucleotide of the target nucleic acid or a second nucleotide of the target nucleic acid according to a degenerate base pairing rule, wherein the two-base degenerate sequence of the target nucleic acid is determined without determining the four-base sequence of the target nucleic acid.

2. The method of claim 1 wherein the two-base degenerate code consists of a first element representing a purine base and a second element representing a pyrimidine base.

3. The method of claim 1 wherein the two-base degenerate code consists of a first element representing a keto base and a second element representing an amino base.

4. The method of claim 1 wherein the two-base degenerate code consists of a first element representing a strongly hydrogen bonding base and a second element representing a weakly hydrogen bonding base.

5. The method of claim 1 wherein the two-base degenerate code consists of a first element representing a base comprising adenine (A) or guanine (G) and a second element representing a base comprising cytosine (C) or thymine (T).

6. The method of claim 1 wherein the two-base degenerate code consists of a first element representing a base comprising A or C and a second element representing a base comprising G or T.

7. The method of claim 1 wherein the two-base degenerate code consists of a first element representing a base comprising G or C and a second element representing a base comprising A or T.

8. The method of claim 1 further comprising using a first two-base degenerate sequence and a second two-base degenerate sequence to produce a four-base sequence.

9. The method of claim 1 wherein the determining comprises measuring a physical, chemical, and/or electronic characteristic of a base and differentiating between a purine base and a pyrimidine base, between a keto base and an amino base, and/or between a strongly hydrogen bonding base and a weakly hydrogen bonding base.

10. The method of claim 1 further comprising comparing the two-base sequence of the target nucleic acid to a known reference sequence.

11. The method of claim 1 further comprising providing a labeled nucleotide analogue wherein the labeled nucleotide analogue base pairs with a first nucleotide or a second nucleotide according to a degenerate base pairing rule.

12. The method of claim 1 further comprising c) comparing the two-base degenerate sequence of the target nucleic acid to a known sequence of the target nucleic acid using the two base degenerate code.

13. A method for sequencing a target nucleic acid, the method comprising:
a) choosing a two-base degenerate code; and
b) sequencing a two-base degenerate sequence of the target nucleic acid using the two-base degenerate code and a first labeled nucleotide analogue and a second labeled nucleotide analogue wherein the first labeled nucleotide analogue base pairs with a first nucleotide of said target nucleic acid or a second nucleotide of said target nucleic acid and the second labeled nucleotide analogue base pairs with a third nucleotide of said target nucleic acid or a fourth nucleotide of said target nucleic acid according to a degenerate base pairing rule, wherein the two-base degenerate sequence of the target nucleic acid is determined without determining the four-base sequence of the target nucleic acid.

* * * * *

SEQUENCE LISTING

<160> NUMBER OF SEQ ID NOS: 11

<210> SEQ ID NO 1
<211> LENGTH: 184
<212> TYPE: DNA
<213> ORGANISM: Homo sapiens

<400> SEQUENCE: 1
aactgagcgg cagcagcgag acctggccta ctgtgtgtca cagctgcccc tcacagagcg    60
aggcctccgt aagatgcttg acaattttga ctgttttgga gacaaactgt cagatgagtc    120
catcttcagt gcttttttgt cagttgtagg caagctgcga cgtggggcca agcctgaggg    180
caag    184

<210> SEQ ID NO 2
<211> LENGTH: 184
<212> TYPE: DNA
<213> ORGANISM: Homo sapiens

<400> SEQUENCE: 2
rryyrrryrr yrryrryrrr ryyyrryyyr yyryryryyr yrryyryyyy yyryrrrryr    60
rrryyyyyry rrrryryyyr ryrryyyyrr yyryyyyrrr rryrrryyry yrrryrrryy    120
yryyyyyrry ryyyyyyyry yrryyryrrr yrrryyryrr yryrrrryyr rryyyrrrrr    180 yrrr    184

<210> SEQ ID NO 3
<211> LENGTH: 184
<212> TYPE: DNA
<213> ORGANISM: Homo sapiens

<400> SEQUENCE: 3 mmkkmkmkk mmkmmkmkmk mmmkkkmmkm mkkkkkkkmm mmkmkkmmmm kmmmmkmkmk    60
mkkmmkmmkk mmkmkkmkkk mmmmkkkkkm mkkkkkkkkm kmmmmmmkkk mmkmkkmkkm    120
mmkmkkmmkk kmkkkkkkkk mmkkkkkmkk mmmkmkkmkm mkkkkkkmmm mkmmkkmkkk    180 mmmk    184

<210> SEQ ID NO 4
<211> LENGTH: 180
<212> TYPE: DNA
<213> ORGANISM: Bacteriophage MS2

<400> SEQUENCE: 4
cttctatcgg attttaagg caaggcaagg gctccgaaaa tatttaaccc ggaggcccgg    60
cagcaatcgc atcaactacc ggcgagctac gaatagacgc cggccaggca aatcattatt   120
acgggaccca gggctaagat caacaaatag gcaaggcggg aggattgatt cgccgctcga   180

<210> SEQ ID NO 5
<211> LENGTH: 180
<212> TYPE: DNA
<213> ORGANISM: Bacteriophage MS2

<400> SEQUENCE: 5
ckkckakckk akkkkkaakk caakkcaakk kckcckaaaa kakkkaaccc kkakkccckk    60
cakcaakckc akcaackacc kkckakckac kaakakackc ckkccakkca aakcakkakk   120
ackkkaccca kkkckaakak caacaaakak kcaakkckkk akkakkkakk ckcckckcka   180

<210> SEQ ID NO 6
<211> LENGTH: 179
<212> TYPE: DNA
<213> ORGANISM: Bacteriophage MS2

<400> SEQUENCE: 6
ckkckakckk akkkkkaakk caakkcaakk kckcckaaaa kakkkaaccc kkakkccckk    60
cakcaakcka kcaackacck kckakckack aakakackcc kkccakkcaa akcakkakka   120
ckkkacccak kkckaakakc aacaaakakk caakkckkka kkakkkakkc kcckckcka    179

<210> SEQ ID NO 7
<211> LENGTH: 177
<212> TYPE: DNA
<213> ORGANISM: Bacteriophage MS2

<400> SEQUENCE: 7
ctgcgagctt attgttaagg caatgcaagg tctcctaaaa gatggaaacc cgattccctc    60
agcaatcgca gcaaactccg gcatctacta atagacgccg gccattcaaa catgaggatt   120
acccatgtcg aagacaacaa agaagttcaa ctctttatgt attgatcttc ctcgcga      177

<210> SEQ ID NO 8
<211> LENGTH: 193
<212> TYPE: DNA
<213> ORGANISM: Bacteriophage MS2

<400> SEQUENCE: 8
agatttaatt acgaacgcca ggcttcgaca ttaagctcga caccaccaac attcgggggg    60
ggcctacgga gggcagcctc gacgggattt ttaggggcta ggggcgggct catatcgcgg   120
acgaagctac atttacgggg aattccgggg aacgcggagg gttattcgat cgctagcgag   180
cccttatcga att                                                     193

<210> SEQ ID NO 9
<211> LENGTH: 193
<212> TYPE: DNA
<213> ORGANISM: Bacteriophage MS2

```
<400> SEQUENCE: 9
akakkkaakk ackaackcca kkckkckaca kkaakckcka caccaccaac akkckkkkkk      60
kkcckackka kkkcakcckc kackkkakkk kkakkkkcka kkkkckkkck cakakckckk     120
ackaakckac akkkackkkk aakkcckkkk aackckkakk kkkakkckak ckckakckak     180
ccckkakcka akk                                                        193

<210> SEQ ID NO 10
<211> LENGTH: 193
<212> TYPE: DNA
<213> ORGANISM: Bacteriophage MS2

<400> SEQUENCE: 10
atatttaagt acgaacgcca tgcggctaca ggaagctcta caccaccaac agtctgggtt     60
gccactttag gcacctcgac tttgatggtg tatttgcgat tctgcgcaga gctctgacga    120
acgctacagg ttactttgta agcctgtgaa cgcgagttag agctgatcca ttcagcgacc    180
ccgttagcga agt                                                        193

<210> SEQ ID NO 11
<211> LENGTH: 193
<212> TYPE: DNA
<213> ORGANISM: Bacteriophage MS2

<400> SEQUENCE: 11
atatttaagt acgaacgcca tgcggctaca ggaagctcta caccaccaac agtctgggtt     60
gccactttag gcacctcgac tttgatggtg tatttgcgat tctgcgcaga gctctgacga    120
acgctacagg ttactttgta agcctgtgaa cgcgagttag agctgatcca ttcagcgacc    180
ccgttagcga agt                                                        193
```